(12) United States Patent
Khambhaty et al.

(10) Patent No.: US 7,951,561 B2
(45) Date of Patent: May 31, 2011

(54) METHOD FOR THE PREPARATION OF κ-CARRAGEENASE

(75) Inventors: Yasmin Najmuddin Khambhaty, Gujarat (IN); Kalpana Haresh Mody, Gujarat (IN); Bhavanath Jha, Gujarat (IN)

(73) Assignee: Council of Scientific and Industrial Research, Rafi Marg, New Delhi (IN)

( * ) Notice: Subject to any disclaimer, the term of this patent is extended or adjusted under 35 U.S.C. 154(b) by 1314 days.

(21) Appl. No.: 11/509,755

(22) Filed: Aug. 25, 2006

(65) Prior Publication Data
US 2007/0231866 A1 Oct. 4, 2007

(30) Foreign Application Priority Data

Mar. 28, 2006 (IN) .............................. 858/DEL/2006

(51) Int. Cl.
*C12P 21/04* (2006.01)
(52) U.S. Cl. ..... 435/71.1; 435/183; 435/200; 435/253.3
(58) Field of Classification Search .................. 435/207, 435/200, 253.3, 71.1, 183
See application file for complete search history.

(56) References Cited

OTHER PUBLICATIONS

Dyrset et al. Enzyme Microb. Technol. (1997) 20:418-423.*
Khambhaty et al. Biotech. Bioprocess. Engineer. (2007) 12: 668-675.*
Greer et al. Can. J. Microbiol. (1994) 30: 1500-1506.*

\* cited by examiner

*Primary Examiner* — Sandra Saucier
*Assistant Examiner* — Susan Hanley
(74) *Attorney, Agent, or Firm* — McDermott Will & Emery LLP

(57) ABSTRACT

Halophilic marine gram negative bacteria, isolated from decayed algae, hydrolyzed κ-carrageenan. To maximize κ-carrageenase production in the cost effective manner, a novel medium was defined having minimum components and their optimum concentration by statistical optimization method. Hence there evolved a novel medium composition for enhanced κ-carrageenase production by a new halotolerant marine bacterium, *Pseudomonas* spp.

4 Claims, No Drawings

METHOD FOR THE PREPARATION OF κ-CARRAGEENASE

This application claims priority to Indian Application No. 0858/DEL2006, filed Mar. 28, 2006.

FIELD OF INVENTION

The present invention relates to a method for the preparation of κ-carrageenase. More particularly, the present invention relates to a method for the preparation of κ-carrageenase by using halotolerant marine gram negative bacteria *Pseudomonas* sp. with accession number MTCC 5261.

BACKGROUND AND PRIOR ART OF THE INVENTION

The potential uses of κ-carrageenase is to obtain low molecular weight carbohydrates, for kelp digestion, for prevention of biofouling by controlling red algal bloom formation, to obtain fine chemicals and for algal biotechnology.

Carrageenan is a natural ingredient obtained from certain species of the red seaweed; class Rhodophyceae (Greer, C. W., and W. Yaphe. 1984. Enzymatic analysis of carrageenans: Structure of carrageenan from *Eucheuma nudum*. Hydrobiologia. 116/117: 563-567). Carrageenan is a linear polysaccharide made up of repeating dissaccharide sequence of 1,3 linked β-D-galactopyranose called the A residue and α-D-galactopyranose residues linked through positions 1,4 called the B residue. Carrageenans are distinguished from agars in that the B units in carrageenan are in the D form whereas they are in the L form in agar. The regular backbone of the basic structure of carrageenan is disrupted by a more or less ordered distribution of sulfate hemi ester groups. Carrageenan can also contain some methoxy and pyruvate groups. Popular sources for carrageenan are *Chondrus*, *Eucheuma* (*Kappaphycus*), *Gigartina* and *Iridaea* species. Three basic types of carrageenan are available. Kappa (κ), iota (ι) and lambda (λ) carrageenan which are obtained from *Chondrus*, *Eucheuma* and *Gigartina* species, which differ in the number and location of sulfate ester substitution. κ and ι-carrageenan form thermally reversible gels in the presence of $K^+$, $Ca^{+2}$ or $NH_4^+$ but do not gel in the $Na^+$ form.

Hydrolases, which degrade carrageenans at β-1,4 linkages, are known as carrageenases. Three types of enzymes, viz. κ, ι and λ-carrageenases, have been isolated from various marine bacteria. They all are endohydrolases that cleave the β-1,4 linkages of carrageenans yielding products of the neo-carrabiose series (Michel, G., L. Chantlat, E. Fanchon, B. Henrissat, B. Kloareg, and O. Didweberg. 2001. The ι-carrageenase of *Alteromonas fortis*. Journal of Biological Chemistry. 276(43): 40202-40209). κ-carrageenase has large-scale application and industrial demand in the forth-coming years (Ostgaard, K., B. F. Wangen, S. H. Knutsen, and I. M. Aasen. 1993. Large scale production and purification of κ-carrageenase from *Pseudomonas carrageenovora* for applications in seaweed biotechnology. Enzyme and Microbial Technology. 15(4): 326-333).

Jhonston and McCandless in a paper entitled "Enzymic hydrolysis of the potassium chloride soluble fraction of carrageenan: properties of λ-carrageenases from—*Pseudomonas carrageenovora*" in Canadian Journal of Microbiology 19: (1973) p.p. 779-788, has reported that carrageenase from *Pseudomonas carrageenovora* exhibited activity only against KCl soluble fraction of carrageenan i.e. λ-carrageenan. They could improve the yield of λ-carrageenase but could not totally eliminate simultaneous production of κ-carrageenase. Also, after using multiple and complicated steps of purification, specific activity achieved was only 7 galactose units/mg protein which had temperature and pH optima 28° C. and 6.2 respectively. The drawback of this work is that carrageenase is active only in acidic condition and at 28° C. temperature. Hence it can not be used in alkaline condition as well as at elevated temperature. Moreover, the process did not yield noteworthy purification of enzyme, in spite of using complicated enzyme purification steps.

Bellion et al. in a paper entitled "The degradation of *Eucheuma spinosum* and *Eucheuma cottoni* carrageenans by ι and κ-carrageenases from marine bacteria" in Canadian Journal of Microbiology 28(7): (1982) p.p. 874-880 has reported the degradation of *Eucheuma spinosum* and *Eucheuma cottonii* carrageenans by ι-carrageenase and κ-carrageenase from marine *Pseudomonas carrageenovora* and identified the hydrolyzed products. The bacterium was cultivated in a medium consisting of g. $l^{-1}$ NaCl 25; $K_2HPO_4$ 0.1; $MgSO_4 7H_2O$ 5.0; $CaCl_2 2H_2O$ 0.2; casamino acids 2.5; carrageenan 2.5; 0.3% $FeSO_4$ (10 ml/lit) and optimum incubation temperature of 22° C. The drawback is that the medium used for the production of carrageenase by this bacterium consisted of 7 components. Moreover, optimum incubation temperature used was 22° C., which is not feasible for the cultivation of this type of bacteria in temperate countries without cooling device especially in summer.

Sarwar et al. in a paper entitled "Potentiality of artificial sea water salts for the production of carrageenase by a marine *Cytophaga* species" in Microbiology and Immunology. 29(5): (1985) p.p. 405-411 and "Purification of a κ-carrageenase from marine *Cytophaga* species" in Microbiology and Immunology. 31(9): (1987) p.p. 869-877 wherein, 8 components were used in the medium for the production of carrageenase by a marine *Cytophaga* sp. Moreover, this culture required a suitable combination of NaCl and $MgCl_2$ for carrageenase production. The pH and temperature optima were 7.6 and 25° C. respectively. The activity achieved after following complicated steps of purification was only 5.0 galactose units/mg protein. The drawback of this work is that the presence of NaCl and $MgCl_2$ in the medium is a must for carrageenase production and inspite of using eight medium components and complicated steps of purification; only 5.0 galactose units/mg protein was obtained as enzyme activity. This low yield makes the enzyme production commercially uneconomical.

Fleurence et al. in a paper entitled "Use of enzymatic cell wall degradation for improvement of protein extraction from *Chondrus crispus*, *Gracilaria verrucosa* and *Palmaria palmata*" in Journal of Applied Phycology 7: (1995) 393-397) wherein, κ-carrageenase was reported to have maximum activity between pH 6.5-6.8 and at 45° C. and lower activity at acidic and alkaline conditions. The drawback of this work is that the enzyme is active only at neutral pH hence can not be used either in acidic and alkaline conditions. Moreover, poor activity at lower temperature makes its applicability limited to higher temperature.

Dyrset et al. in a paper entitled "Development of a fermentation process for production of a κ-carrageenase from *Pseudomonas carrageenovora*" in Enzyme and Microbial Technology 20(6): (1997) p.p. 418-423 has reported a fermentation process for the production of κ-carrageenase using two strains of *Pseudomonas carrageenovora*. The medium used for this study contained $gl^{-1}$ of $CaCl_2$, $2H_2O$ 0.2; Casamino acid 6.8; KCl 0.3; $K_2HPO_4$ 3.0; $MgSO_4$, $7H_2O$ 0.5; NaCl 20.0; $NH_4Cl$ 0.7; $(NH_4)_2 SO_4$ 5.0; Carrageenan 2.5. The pH of the medium was 7.0 and temperature was 20° C. The drawback of this work is that large number of components as well as high substrate concentration is required in the medium and the maintenance of pH 7.0 with all these components is difficult. Besides, the fermentation process is carried out at 20° C., which requires special device for maintaining such low temperature Araki et al. in a paper entitled "Purification and characterization of κ-carrageenase form a marine bacterium *Vibrio* sp. CA-, 1004" in Fisheries Science 65 (6): (1999) p.p. 937-942 wherein, they purified and characterized κ-carrageenase, an inducible enzyme, from a marine bacterium *Vibrio* species, the molecular weight of which was 35 KDa and maximum enzyme activity at pH 8.0 and temperature 40° C. The medium used for this study contained g $1^{-1}$ of peptone 5.0; yeast extract 1.0; NaCl 30; $MgSO_4$ 0.5; $K_2HPO_4$ 2.0; $KH_2PO_4$ 0.4; carrageenan 15. The activity of crude carrageenase obtained was 0.949 galactose units/mg protein. The drawback of this work is that production medium containing seven components yielded carrageenase with activity of only 0.949 galactose units/mg protein. Such low activity would invariably make the process uneconomical and unfeasible.

Japanese patent No. JP2001136961 (2001) assigned to Okita Yuji et al. has disclosed a "Method for controlling carrageenase producing ability of bacterium" is described. Here, a method has been described to control the carrageenase producing ability of a carrageenase producing bacterium, by culturing it in the presence of a bacterium free from the carrageenase producing ability or its culture product. The drawback of this invention is that production of carrageenase was controlled only by co-cultivating carrageenase producer with that of carrageenase non producer.

Japanese patent No. JP 2000116376 (2000) assigned to Araki Toshiyoshi entitled "New κ-carrageenase, microorganism for producing the same, production of carrageenase and its use" has disclosed that κ-carrageenase has decomposition activity against κ-carrageenan. This enzyme decomposed κ-carrageenan into neocarrabiose and neocarratetraose and had pH optima of 8.0. The drawback of this invention is that the enzyme had only alkaline pH optima hence can not be used in acidic condition.

Japanese patent No. JP1006656 (1998) assigned to Christian G et al. entitled "Production of κ-carrageenase" has disclosed the productivity of κ-carrageenase by *Pseudomonas carrageenovora, Alteromonas* or *Cytophoga* which was substantially improved by controlling the pH of a culture medium by nitrogen containing base (ammonium water) to be assimilated by these bacteria. By this, κ-carrageenase production could be improved from >=20 galactose Units/ml to 40 to 60 galactose Units/ml. The drawback of this invention is that they could achieve only 3fold purification after controlling pH which is not viable commercially.

Canadian Patent No. CN1544623 (2004) assigned to Haigin M et al. entitled "Carrageenin catabolic enzymes it's preparing process and application", wherein, an enzyme that can degrade κ-carrageenan to prepare oligocarrageenan and degrade beta-1,4 indican bond of κ-carrageenan having a molecular weight of 30 KDa was obtained. *Cytophaga* sp. was cultured at 28-35 deg. C., centrifuged to obtain crude enzyme and concentrated it by using 40-80% ammonium sulphate. This method was compared with chemical method; it had simple preparing course, high product yield, and stable quality and ensure the activity research and development of oligosaccharide etc. The drawback of the present invention is that only salting out method was used for concentrating enzyme which does not give substantially concentrated/purified enzyme preparation.

OBJECTS OF THE INVENTION

The main object of the present invention is to provide a method for the preparation of κ-carrageenase.

Another object of the present invention is to provide a method for the preparation of κ-carrageenase by using halotolerant marine gram negative bacteria.

Further another object of the present invention is to provide an improved κ-carrageenase by using halotolerant marine gram negative bacteria which grows in a novel medium composition with optimum concentration.

Yet another object of the present invention is to maximize carrageenase production in a simple manner involving less complicated techniques.

Yet another object of the present invention is to provide κ-carrageenase having excellent κ-carrageenan hydrolyzing activity.

Yet another object of the present investigation is to obtain κ-carrageenase having activity in alkaline and acidic conditions.

Yet another object of the present investigation is to obtain κ-carrageenase having higher temperature stability.

Yet another object of the present investigation is to obtain κ-carrageenase having high substrate specificity.

Yet another object of the present investigation is to obtain κ-carrageenase having prolonged storage stability.

Yet another object of the present investigation is to obtain κ-carrageenase having capability to generate protoplast of *Kappaphycus alvarezii*.

SUMMARY OF THE INVENTION

The present invention deals with a novel halotolerant marine bacterium, *Pseudomonas* spp. with accession no MTCC 5261 deposited under the Budapest Treaty on Jan. 25, 2006, with the Microbial Type Culture Collection and Gene Bank (MTCC), Institute of Microbial Technology, Sector 39-A, Chandigarh-160036, India, with an identification reference of "*Pseudomonas* elongate/Microbulbifer alongatus YK-C-1" useful for the production of high activity κ-carrageenase. In order to maximize κ-carrageenase production in a simple manner, a new medium composition is defined having minimum components and their optimum concentration using statistical optimization method to reduce number of experiments, save time and chemicals and to improve higher authenticity of the results by observing combined effect of all the factors influencing enzyme production.

DETAILED DESCRIPTION OF THE INVENTION

Accordingly, the present invention provides a method for the preparation of κ-carrageenase, wherein the said method comprising the steps of:

(i) growing the halotolerant marine bacterium, *Pseudomonas* sp. with accession number MTCC 5261 in a liquid medium comprises carrageenan, yeast extract, sodium chloride, $K_2HPO_4$ and $KH_2PO_4$ in the ratio ranging from 0.1:1.0:50:1:0.5 to 3.0:1.0:15.0:0.5:0.05 respectively for 16-72 hours at 15-50° C. to obtain culture;

(ii) centrifuging the culture obtained from step (i) at 5000-8000 rpm for 20-40 min to obtain cell free extract as supernatant;

(iv) purifying the crude enzyme from supernatant obtained from step (ii) by treating it with ammonium sulphate at a temperature in the range of 3-15° C. and aging the mixture for a period in the range of 12-36 hours followed by centrifugation at 5000-8000 rpm at 3-15° C. to get the pellet containing κ-carrageenase;

(v) suspending the pellets obtained from step (iv) in Tris-HCl buffer solution;

(v) dialyzing the suspension obtained in step (v) for removing the adhered ammonium sulphate followed by gel filtration to get desired purified κ-carrageenase.

In an embodiment of the present invention, the said bacterium, *Pseudomonas* sp have the following characteristics:
a) halophilic;
b) gram negative, exhibits gram variability;
c) motile aerobic rods;
d) it degrades algal polysaccharide i.e. κ-carrageenan.

In another embodiment of the present invention, the said κ-carrageenase is purified using gel filtration technique on Sepharose CL-4B.

Further, in another embodiment of the present invention, the specific activity of said κ-carrageenase is in the range of 10-200 galactose units/mg protein.

Yet in another embodiment of the present invention, the said κ-carrageenase have the molecular weight 128 KDa.

Still in another embodiment of the present invention, the said κ-carrageenase have excellent κ-carrageenan hydrolyzing activity.

Still in another embodiment of the present invention, the said κ-carrageenase have activity in alkaline and acidic conditions.

Still in another embodiment of the present invention, the said κ-carrageenase have higher temperature stability.

Still in another embodiment of the present invention, the said κ-carrageenase have high substrate specificity.

Still in another embodiment of the present invention, the said κ-carrageenase have prolonged storage stability.

Still in another embodiment of the present invention, κ-carrageenase having capability to generate protoplast of *Kappaphycus alvarezii*

The present invention provides a process for improved κ-carrageenase production and method for preparation thereof which comprises of the isolation of marine bacterial cultures from seawater and sediment located in the vicinity of red algae and decayed carrageenophyte. These bacteria were grown on a solid culture medium containing carrageenan as the only carbon source. Bacterial colonies producing pits or holes in the above said solid medium were further purified and the bacterium producing maximum depression was selected for further studies.

The purified bacterium was then inoculated in a liquid medium containing components in the concentration preferably in range of (g 100 ml$^{-1}$) (i) carrageenan 0.005-6.0 (ii) yeast extract 0.0051-3.0 (iii) sodium chloride 0.1-20.0 (iv) $K_2HPO_4$ 0.001-1.5 (v) $KH_2PO_4$ 0.001-0.1 for its cultivation. The inoculated liquid culture medium was incubated on a rotary shaker for a period in the range of 12-90 hours and temperature in the range of 10-60° C. for production of κ-carrageenase. The cultivated culture suspension was then centrifuging preferably in the range of 4000-10000 rpm for a period in the range of 20-70 minutes to obtain crude extracellular κ-carrageenase as supernatant (cell free extract).

The extracellular crude enzyme (supernatant) was then partially purified by salting out method, using preferably ammonium sulfate in the concentration range of 10-100% (wt/vol) and at a temperature in the range of 3-10° C. and aging the mixture for a period in the range of 12-36 hours to eliminate majority of unwanted protein impurities. This suspension containing ammonium sulfate precipitated proteins was centrifuged preferably in the range of 4000-10000 rpm and at a temperature in the range of 3-10° C. to obtain pellets containing mainly κ-carrageenase and discarding the supernatant containing other protein impurities. The pellets obtained by centrifugation (containing mainly κ-carrageenase) were re suspended in minimum volume of preferably 5-40 mM Tris HCl buffer solution. For the removal of excess ammonium sulfate and other low molecular weight impurities including proteins the partially purified κ-carrageenase solution was dialyzed against 0.02 mM Tris HCl buffer using dialysis bag having 12,000 molecular weight cutoffs.

For further purification of ammonium sulfate precipitated κ-carrageenase, gel filtration technique on Sepharose CL-4B was used and κ-carrageenase rich fractions were recovered by eluting them using Tris HCl buffer preferably in the concentration range of 5-50 mM. The molecular weight of purified κ-carrageenase fraction was determined by repeated gel filtration method, noting its elution volume (Ve), calculating its Ve/Vo (Vo is void volume of the column) and comparing it with a plot of log of molecular weight Vs Ve/Vo of standard molecular weight proteins markers.

Potential uses of this enzyme are as follows:
To improve the physical properties of polysaccharides, conversion to oligosaccharide may be the best choice. The enzymatic degradation of carrageenan yields novel products with high bioactivity.

The enzymes produced by marine bacteria could effectively control red algal bloom contamination. Thus, it prevents bio fouling of submerged marine surface or pipes by acting on complex polysaccharide layers.

These enzymes are essential tools to study structure and assembly of red algal cell walls (Gall, Y. L., J. P. Braud and B. Kloareg. 1990. Protoplast production in *Chondrus crispus* gametophytes (Gigartinales, Rhodophyta). Plant Cell Reports. 8: 582-585).

These enzymes are useful for kelp digestion (Sarwar, G., H. Oda, T. Sakata, and D. Kakimoto. 1985. Potentiality of artificial sea water salts for the production of carrageenase by a marine *Cytophaga* species. Microbiology Immunology. 29(5): 405-411). The digested products in turn can be used as carbon source for the growth of bacteria. They are also used for the extraction of fine chemicals from these algae.

Most red seaweed possesses high level of proteins (10-30% dry weight) (Morgan, C., J. L. C. Wright and J. Simpson. 1980. Review of chemical constituents of the red alga *Palmaria palmate* (dulse). Economic Botany. 34: 27-50; Mabeau, S., and J. Fleurence. 1993. Seaweed in food products: biochemical and nutritional aspects. Trends Foods Science & Technology. 4: 103-107). These proteins can be extracted by hydrolytic enzymes like carrageenase (Fleurence, J., L. Massiani, O. Guyader, and S. Mabeau. 1995. Use of enzymatic cell wall degradation for improvement of protein extraction from *Chondrus crispus, Gracilaria verrucosa* and *Palmaria palmate*. Journal of Applied Phycology. 7: 393-397). For example, the degradation of cell wall polysaccharides by hydrolytic enzymes is used for the isolation of extensin, a protein linked to cell wall polysaccharide of higher plants (Lamport, D. T. A. 1969. The isolation and partial characterization of hydrodyproline rich glycolipides obtained by enzymic degradation on primary cell walls. Biochemistry. 3: 1155-1163).

They can be used for the isolation of protoplast, which can be used for genetic engineering experiments for the production of improved algal strains (Chen, L. C. M., J. S. Craigie, and Z. K. Xie. 1994. Protoplast production from *Porphyra linearis* using a simplified agarase procedure capable of commercial application. Journal of Applied Phycology. 6: 35-39).

They are used in molecular biology to prevent severe separation problems occurring in the presence of phycocolloids. They are also used for production of defined phycocolloid oligomers for pharmacy and immunology (Dyrset, N., K. Q. Lystad, and D. W. Levine. 1997. Development of a fermentation process for production of a κ-carrageenase from *Pseudomonas carrageenovora*. Enzyme and Microbial Technology. 20(6): 418-423).

Carrageenases provide the opportunity to investigate the structure-function relationships of the hydrolases that degrade self-associating sulfated polysaccharides (Michel, G., L. Chantlat, E. Fanchon, B. Henrissat, B. Kloareg, and O. Didweberg. 2001. The ι-carrageenase of *Alteromonas fortis*. Journal of Biological Chemistry. 276(43): 40202-40209).

According to the present invention, it is provided with an indigenous, novel halotolerant marine bacterium, identified as *Pseudomonas* spp, having a potency of degrading κ-carrageenan into lower molecular weight substances. The present invention also relates to a novel medium composition used for maximizing production of κ-carrageenase having following physicochemical properties (1) Optimum substrate concentration: 0.02%; (2) Optimum temperature: 40° C.; (3) Heat stability: between 20-50° C.; (4) Optimum pH: 5.6 and 7.7; (5) Substrate specificity: highly specific to κ-carrageenan, does not hydrolyze λ and ι carrageenan and LMP agarose; (6) Storage stability: for a period of 15 days when stored at −20° C.; sensitive to freezing & thawing (7) Solubility: soluble in water; (8) Molecular weight: The molecular weight was determined by SDS polyacrylamide gel electrophoresis (SDS PAGE), with the result that the molecular weight is 128 KDa. No report is available on κ-carrageenase having such a high molecular weight.

According to the present invention, still furthermore, it is provided a method for preparing protoplast of *Kappaphycus alvarezii* using κ-carrageenase.

In the present invention, for the first time, a novel halotolerant marine bacterium, *Pseudomonas* spp., was isolated, from West coast of India, having the potency of producing κ-carrageenase. In order to maximize κ-carrageenase production, a novel medium composition was defined having minimum components and their optimum concentration using statistical optimization method. By following statistical optimization it was feasible to increase the specific activity of crude κ-carrageenase by 32 fold.

The inventive steps adopted in the present invention are (i) the process alleviate the need of multi-steps for the purification of enzymes; (ii) the wide pH range from 4 to 10 in the present invention is feasible to achieve high specific activity of κ-carrageenase; (iii) the culture medium dispenses the need of multiple components; (iv) the process utilizes minimum concentration of substrate in the culture medium essential for enzyme induction; (v) the process dispenses the need of low temperature (20° C.) for maximum recovery of κ-carrageenase; (vi) maximum κ-carrageenase can be recovered at a wide range of temperature between 25° C. to 50° C.; (vii) the components in the culture medium dispenses the need of co-cultivating carrageenan producers with that of carrageenase non-producers to control κ-carrageenase production.

The following examples are given by way of illustration of the present invention and should not be construed to limit the scope of present invention.

Example 1

The isolated *Pseudomonas* spp. was inoculated in a 250 ml conical flask containing 100 ml of liquid medium comprising of (g. 100 ml$^{-1}$) carrageenan—0.003, yeast extract—0.01, sodium chloride—0.3, dipotassium hydrogen phosphate—0.04 and potassium dihydrogen phosphate—0.003 at pH 6.3. This was incubated at 30° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 50% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were re suspended in 10 mM Tris-HCl buffer and dialyzed against the same buffer. The partially purified enzyme was further purified using gel filtration technique which yielded a specific activity of 9.2 galactose units/mg protein.

Example 2

The isolated *Pseudomonas* spp. was inoculated in a 250 ml conical flask containing 100 ml of liquid medium comprising of (g. 100 ml$^{-1}$) carrageenan—0.03, yeast extract—0.01, sodium chloride—0.3, dipotassium hydrogen phosphate—0.004 and potassium dihydrogen phosphate—0.03 at pH 8.4. This was incubated at 30° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 40% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 15 mM Tris-HCl buffer and dialyzed against the same buffer. The partially purified enzyme was further purified using gel filtration technique which yielded a specific activity of 8.4 galactose units/mg protein

Example 3

The isolated *Pseudomonas* spp. was inoculated in a 250 ml conical flask containing 100 ml of liquid medium comprising of (g. 100 ml$^{-1}$) carrageenan—0.03, yeast extract—0.1, sodium chloride—0.3, dipotassium hydrogen phosphate—0.004 and potassium dihydrogen phosphate—0.003 at pH 5.1. This was incubated at 35° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 55% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 20 mM Tris-HCl buffer and dialyzed against the same buffer. The partially purified enzyme was further purified using gel filtration technique which yielded a specific activity of 24.2 galactose units/mg protein.

Example 4

The isolated *Pseudomonas* spp. was inoculated in a 250 ml conical flask containing 100 ml of liquid medium comprising of (g. 100 ml$^{-1}$) carrageenan—0.03, yeast extract—0.1, sodium chloride—3.0, dipotassium hydrogen phosphate—0.004 and potassium dihydrogen phosphate—0.003 at pH 8.0. This was incubated at 40° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 70% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 25 mM Tris-HCl buffer and dialyzed against the same buffer. The partially purified enzyme was further purified using gel filtration technique which yielded a specific activity of 10.5 galactose units/mg protein.

Example 5

The isolated *Pseudomonas* spp. was inoculated in a 250 ml conical flask containing 100 ml of liquid medium comprising of (g. 100 ml$^{-1}$) carrageenan—0.003, yeast extract—0.1, sodium chloride—3.0, dipotassium hydrogen phosphate—0.04 and potassium dihydrogen phosphate—0.003 at pH 8.4. This was incubated at 25° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 30% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 15 mM Tris-HCl buffer and dialyzed against the same buffer. The partially purified enzyme was further purified using gel filtration technique which yielded a specific activity of 16.2 galactose units/mg protein.

Example 6

The isolated *Pseudomonas* spp. was inoculated in a 250 ml conical flask containing 100 ml of liquid medium comprising of (g. 100 ml$^{-1}$) carrageenan—0.03, yeast extract—0.01, sodium chloride—3.0, dipotassium hydrogen phosphate—0.04 and potassium dihydrogen phosphate—0.03 at pH 7.1. This was incubated at 25° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 40% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 15 mM Tris-HCl buffer and dialyzed against the same buffer. The partially purified enzyme was further purified using gel filtration technique which yielded a specific activity of 14.8 galactose units/mg protein.

Example 7

The isolated *Pseudomonas* spp. was inoculated in a 250 ml conical flask containing 100 ml of liquid medium comprising of (g. 100 ml$^{-1}$) carrageenan—0.03, yeast extract—0.1, sodium chloride—0.3, dipotassium hydrogen phosphate—0.04 and potassium dihydrogen phosphate—0.03 at pH 9.0. This was incubated at 40° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 75% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 30 mM Tris-HCl buffer and dialyzed against the same buffer. The partially purified enzyme was further purified using gel filtration technique which yielded a specific activity of 8.9 galactose units/mg protein.

Example 8

The isolated *Pseudomonas* spp. was inoculated in a 250 ml conical flask containing 100 ml of liquid medium comprising of (g. 100 m$^{-1}$) carrageenan—0.003, yeast extract—0.1, sodium chloride—3.0, dipotassium hydrogen phosphate—0.004 and potassium dihydrogen phosphate—0.03 at pH 7.1. This was incubated at 30° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 65% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 25 mM Tris-HCl buffer and dialyzed against the same buffer. The partially purified enzyme was further purified using gel filtration technique which yielded a specific activity of 11.4 galactose units/mg protein.

Example 9

The isolated *Pseudomonas* spp. was inoculated in a 250 ml conical flask containing 100 ml of liquid medium comprising of (g. 100 ml$^{-1}$) carrageenan—0.03, yeast extract—0.01, sodium chloride—3.0, dipotassium hydrogen phosphate—0.04 and potassium dihydrogen phosphate—0.003 at pH 6.3. This was incubated at 30° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 55% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 15 mM Tris-HCl buffer and dialyzed against the same buffer. The partially purified enzyme was further purified using gel filtration technique which yielded a specific activity of 11.8 galactose units/mg protein.

Example 10

The isolated *Pseudomonas* spp. was inoculated in a 250 ml conical flask containing 100 ml of liquid medium comprising of (g. 100 ml$^{-1}$) carrageenan—0.003, yeast extract—0.1, sodium chloride—0.3, dipotassium hydrogen phosphate—0.04 and potassium dihydrogen phosphate—0.03 at pH 5.1. This was incubated at 35° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 35% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 25 mM Tris-HCl buffer and dialyzed against the same buffer. The partially purified enzyme was further purified using gel filtration technique which yielded a specific activity of 17.3 galactose units/mg protein.

Example 11

The isolated *Pseudomonas* spp. was inoculated in a 250 ml conical flask containing 100 ml of liquid medium comprising of (g. 100 ml$^{-1}$) carrageenan—0.003, yeast extract—0.01, sodium chloride—3.0, dipotassium hydrogen phosphate—0.004 and potassium dihydrogen phosphate—0.03 at pH 4.5. This was incubated at 40° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 70% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 30 mM Tris-HCl buffer and dialyzed against the same buffer. The partially purified enzyme was further purified using gel filtration technique which yielded a specific activity of 5.9 galactose units/mg protein.

Example 12

The isolated *Pseudomonas* spp. was inoculated in a 250 ml conical flask containing 100 ml of liquid medium comprising of (g. 100 ml$^{-1}$) carrageenan—0.003, yeast extract—0.01, sodium chloride—0.3, dipotassium hydrogen phosphate—0.004 and potassium dihydrogen phosphate—0.003 at pH 5.1. This was incubated at 35° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 40% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 15 mM Tris-HCl buffer and dialyzed against the same buffer. The partially purified enzyme was further purified using gel filtration technique which yielded a specific activity of 17.4 galactose units/mg protein.

Example 13

The isolated *Pseudomonas* spp. was inoculated in a 250 ml conical flask containing 100 ml of liquid medium comprising of (g. 100 ml$^{-1}$) carrageenan—0.3, yeast extract—0.04, sodium chloride—3.0, dipotassium hydrogen phosphate—0.03 and potassium dihydrogen phosphate—0.01 at pH 5.6. This was incubated at 35° C. on rotary shaker at 180 rpm (rev/min) for a period of 28 hours. The crude carrageenase was obtained as cell free extract after centrifuging the suspension at 8000 rpm for 15 minutes. This crude carrageenase was partially purified by treatment with 60% ammonium sulphate (wt/vol) at a temperature of 4° C. and aging the mixture for 24 hours. After incubation, the solution was centrifuged at 8000 rpm at 4° C. for 15 minutes to obtain pellets of precipitated protein. The obtained pellets were resuspended in 20 mM Tris-HCl buffer and dialyzed against the same buffer. The partially purified enzyme was further purified using gel filtration technique which yielded an enzyme fraction having specific activity of 188.8 galactose units/mg protein.

Advantages:

The main advantages of the present invention are:
1. In order to maximize kappa carrageenase production in a simple manner, a novel medium composition for growth of novel bacterium is defined having minimal components and their optimum concentration using statistical optimization method to reduce number of experiments, save time and chemicals and to improve higher authenticity of the results by observing combined effect to all the factors influencing enzyme production.
2. The present invention provides κ-carrageenase with high specific activity upto 200 galactose units/mg protein.
3. The present κ-carrageenase have the molecular weight 128 KDa.
4. The present κ-carrageenase have excellent κ-carrageenan hydrolyzing activity.
5. The present κ-carrageenase have activity in alkaline and acidic conditions.
6. The present κ-carrageenase have higher temperature stability.
7. The present κ-carrageenase have high substrate specificity.
8. The present κ-carrageenase have prolonged storage stability.
9. The present κ-carrageenase have capability to generate protoplast of *Kappaphycus alvarezii*

We claim:

1. A method for the preparation of κ-carrageenase, said method comprising the steps of:
   (i) growing a halotolerant marine bacterium, *Pseudomonas* sp., accession number MTCC 5261, in a liquid medium comprising carrageenan, yeast extract, sodium chloride, $K_2HPO_4$ and $KH_2PO_4$ in a concentration ratio ranging from 0.1:1.0:50:1:0.5 to 3.0:1.0:15.0:0.5:0.05, respectively, for 16-72 hours at 15-500° C. to obtain a culture;
   (ii) centrifuging the culture obtained from step (i) at 5000-8000 rpm for 20-40 min. to obtain a cell free extract as a supernatant;
   (iii) treating the supernatant obtained from step (ii) with ammonium sulphate at a temperature in the range of 3-15° C. and aging the mixture for a period in the range of 12-36 hours followed by centrifugation at 5000-8000 rpm at 3-15° C. to obtain a pellet containing κ-carrageenase;
   (iv) suspending the pellet obtained from step (iii) in Tris-HCl buffer solution to obtain a suspension containing κ-carrageenase; and
   (v) dialyzing the suspension obtained in step (iv) for removing adhered ammonium sulphate followed by gel filtration to obtain purified κ-carrageenase.

2. The method as claimed in claim 1 wherein said bacterium, *Pseudomonas* sp., accession number MTCC 5261, has the following characteristics:
   a) said bacterium is halophilic;
   b) said bacterium is gram negative and exhibits gram variability;
   c) said bacterium is the form of motile aerobic rods;
   d) said bacterium degrades algal polysaccharide.

3. The method as claimed in claim 1, wherein the specific activity of said κ-carrageenase is in the range of 10-200 galactose units/mg protein.

4. The method as claimed in claim 1, wherein said κ-carrageenase has a molecular weight of 128 KDa determined by SDS polyacrylamide gel electrophoresis (SDS PAGE).

* * * * *

UNITED STATES PATENT AND TRADEMARK OFFICE
CERTIFICATE OF CORRECTION

| | | |
|---|---|---|
| PATENT NO. | : 7,951,561 B2 | Page 1 of 1 |
| APPLICATION NO. | : 11/509755 | |
| DATED | : May 31, 2011 | |
| INVENTOR(S) | : Khambhaty et al. | |

It is certified that error appears in the above-identified patent and that said Letters Patent is hereby corrected as shown below:

IN THE SPECIFICATION:

Column 1, Line 5:   Replace "0858/DEU2006", with -- 0858/DEL/2006 --

Column 3, Line 48:  Replace "Canadian", with -- Chinese --

Signed and Sealed this
Sixth Day of December, 2011

David J. Kappos
*Director of the United States Patent and Trademark Office*